(12) United States Patent
Hartwich et al.

(10) Patent No.: US 7,045,362 B2
(45) Date of Patent: May 16, 2006

(54) DEVICE AND METHOD FOR DETECTING ORGANIC MOLECULES IN A TEST SUBSTANCE

(75) Inventors: Gerhard Hartwich, München (DE); Harald Lossau, München (DE)

(73) Assignee: Harald Lossau, Munich (DE)

( * ) Notice: Subject to any disclaimer, the term of this patent is extended or adjusted under 35 U.S.C. 154(b) by 622 days.

(21) Appl. No.: 10/220,235

(22) PCT Filed: Feb. 15, 2001

(86) PCT No.: PCT/DE01/00571

§ 371 (c)(1),
(2), (4) Date: Aug. 27, 2002

(87) PCT Pub. No.: WO01/69210

PCT Pub. Date: Sep. 20, 2001

(65) Prior Publication Data

US 2003/0035109 A1    Feb. 20, 2003

(30) Foreign Application Priority Data

Mar. 17, 2000 (DE) ............... 100 13 254

(51) Int. Cl.
*G01N 21/64* (2006.01)
(52) U.S. Cl. ............ 436/172; 436/422; 436/82.08
(58) Field of Classification Search ............ 422/82.05, 422/82.08, 82.01, 82.02; 436/94, 164, 172, 436/149, 151; 250/458.1, 459.1
See application file for complete search history.

(56) References Cited

U.S. PATENT DOCUMENTS

| | | | |
|---|---|---|---|
| 3,013,467 A | 12/1961 | Minsky | |
| 5,500,188 A | 3/1996 | Hafeman et al. | |
| 5,545,531 A | 8/1996 | Rava et al. | |
| 5,578,832 A | 11/1996 | Trulson et al. | |
| 5,631,734 A | 5/1997 | Stern et al. | |
| 5,736,410 A | 4/1998 | Zarling et al. | |
| 5,936,730 A | 8/1999 | Foley et al. | |
| 5,985,568 A | 11/1999 | Krihak et al. | |
| 6,203,985 B1 * | 3/2001 | Jiang et al. ............ | 435/6 |

FOREIGN PATENT DOCUMENTS

| | | |
|---|---|---|
| DE | 38 33 064 A1 | 4/1990 |
| DE | 40 15 930 A1 | 11/1990 |
| DE | 197 31 078 A1 | 12/1998 |
| DE | 197 36 641 A1 | 3/1999 |
| DE | 199 40 751 A1 | 3/2000 |
| DE | 199 40 752 A1 | 4/2000 |
| DE | 199 21 940 A1 | 6/2000 |
| DE | 199 26 457 A1 | 7/2000 |
| DE | 199 45 398 A1 | 4/2001 |
| EP | 0 751 393 A2 | 1/1997 |
| JP | 11094747 A | 4/1999 |
| WO | WO 99/47964 | 9/1999 |
| WO | WO 00/13784 | 3/2000 |

* cited by examiner

*Primary Examiner*—Jeffrey R. Snay
(74) *Attorney, Agent, or Firm*—Squire, Sanders & Dempsey (57) ABSTRACT

An apparatus for detecting organic molecules, especially biomolecules and polymers, in a probe substance, comprises a test system (300) comprising an array of test sites (T) to which the probe substance can be supplied, each test site having specific probe molecules (320), an illumination system (100) for optically illuminating a sub-array of test sites (T), and a detection system (400) for identifying those test sites (T) whose probe molecules (320) interact with the organic molecules (350) to be detected, the illumination system (100) comprising an array of independently addressable illumination sources (B) arranged such that to each test site (T) of the sub-array is assigned at least one illumination source (B) that illuminates substantially only it.

27 Claims, 9 Drawing Sheets

DEVICE AND METHOD FOR DETECTING ORGANIC MOLECULES IN A TEST SUBSTANCE

FIELD OF THE INVENTION

The present invention relates to an apparatus and a method for detecting organic molecules, especially biomolecules and polymers, in a probe substance.

BACKGROUND OF THE INVENTION

Biochips are used particularly in the DNA chip and protein chip embodiments in biotechnology and genetic research. They are ascribed great potential in medical diagnostics, pharmacological and toxicological test procedures, and in the agricultural sector.

A biochip typically includes a two-dimensional array of regions having organic molecules (probes) that are immobilized on a surface and that can specifically react with chemical substances comprising a probe substance (targets). The objective here is the parallel detection of many interactions between probes and targets. When illuminated, photosensitive biochips exhibit a physical reaction that specifically depends on the interaction between probes and targets.

Detection of these interactions occurs, for example, by optical, autoradiographical, mass-spectroscopic, or electrical methods. In doing so, it is necessary to spatially address the various probes on the array. Optical (luminescence) and electrical detection methods, in particular, are known to date within the group of photosensitive biochips. For these chips, addressing can be achieved through spatially restricted optical excitation.

Laser scanners or confocal microscopes have been employed to date for optical excitation. The critical parameters here are uniformity and reproducibility across the entire spatial readout region of the chip. Because of these requirements, the original confocal construction by Minsky (U.S. Pat. No. 3,013,467) is often used as the basis for readout devices., for example as described in U.S. Pat. No. 5,631,734 and U.S. Pat. No. 5,578,832. It consists of an xyz translation table that can be moved below a confocal microscope. In JP11094747, a rotating table is used instead of a translation table. In these methods, the biochip must withstand the occurring acceleration of the table. This ultimately determines the time span in which the chip can be read out. For example, the readout process for a 22×60 mm scan region with a resolution of 10 μm takes about half an hour.

Other optical readout systems, such as that described in WO09947964A1, are based on movable optical components, which make the construction expensive and/or susceptible to interference.

A special readout system for photosensitive biochips with electrical readout is not known to date.

Disadvantages of all known scanning systems are that they are mechanically vulnerable, relatively large, and expensive.

DESCRIPTION OF THE INVENTION

Therefore, it is the object of the present invention to provide an apparatus and a method for detecting organic molecules, especially biomolecules and polymers, in a probe substance or their effect on a test system, that do not exhibit the disadvantages of the prior art.

According to the present invention, this object is solved by the apparatus according to independent claim 1 and the method according to independent claim 12. Preferred embodiments are the subject-matter of the dependent claims.

The apparatus according to the present invention comprises a test system comprising an array of test sites to which the probe substance can be supplied, an illumination system, and a detection system.

Test System

In the present description, the term "biochip" is used for a test system comprising a two-dimensional array of test sites, wherein each test site has specific probe molecules. The probe molecules are immobilized on a surface and can specifically react with chemical substances comprised in a probe substance (targets). The objective here is the parallel detection of many interactions between probes and targets.

The term "probe molecules" includes especially biomolecules, polymers, and their complexes with other chemical substances, especially biomolecules, polymers, dyes, metals, and redoxactive substances. Probe molecules comprise preferably DNA, RNA, or PNA fragments (DNA—deoxyribonucleic acid, RNA—ribonucleic acid, PNA—peptide nucleic acid: synthetic DNA or RNA in which the sugar-phosphate moiety is replaced by an amino acid). In these cases, the corresponding biochip is referred to as a DNA chip. Probe molecules comprising proteins (term for the corresponding biochip: protein chip) or glucose compounds (glucose chip) are likewise preferred. Furthermore, the probe molecules can especially include labeling substances, especially dyes or redoxactive substances, and linkers (molecule groups that serve to link or attach molecular moieties).

"Targets" are understood to be organic molecules in the probe substance, especially biomolecules, polymers, drugs, or other active substances that can specifically interact with the probe molecules.

Within the context of the present invention, a biochip is referred to as photosensitive if a physical reaction that specifically depends on the interaction between probes and targets is caused by spatially limitable illuminating, and optical addressing of the array elements (test sites) is possible.

To be able to supply the probe substance to the biochip, a supply apparatus is employed. Both independent supply apparatuses, especially syringes, pipettes, tubing, cannula, piping, and funnels, and apparatuses connected with the test system may be considered. The latter can be integrated into the casing of the test system and can effect protection of the test system from interference factors such as impurities, mechanical stress, temperature differences, and evaporation, as well as facilitate sparing use of the probe substance.

Illumination System

Within the context of the present invention, an "illumination system" is understood to be one or more illumination sources that are suitable for initiating a physical reaction on a photosensitive biochip. According to the present invention, the illumination system comprises an array of independently addressable illumination sources that are arranged such that to each test site of a sub-array of the test system is assigned at least one illumination source that illuminates substantially only it.

In addition, the illumination system can include an optical projection system for imaging the array of illumination sources on the test system in such a way that, on each test site of the sub-array, at least one illumination source assigned to it can be imaged.

A "projection system" is understood to be any system suitable for optical imaging, especially consisting of lenses and/or mirrors. The projection system can include additional optical components, especially filters, apertures, polarizers, and beam splitters. In the narrower sense, a projection system within the context of the present invention is understood to be an optical system for imaging illumination sources on a photosensitive biochip.

As an alternative to providing a projection system, the array of illumination sources can be arranged substantially parallel to the test system and at such a short distance therefrom that the radiation emitted from each illumination source illuminates substantially only the test site assigned to it. In this case, a projection system is not required.

Here, the array of illumination sources can consist especially of one or more of the following components: a cathode ray tube (CRT), a liquid crystal device/display (LCD)—which is preferably addressed by an active matrix comprising thin film transistors (TFT), a spatial light modulator (SLM), especially a digital micromirror device (DMD—an array of independently addressable micromirrors), light emitting diodes (LED), a polymer display (OLED—organic LED), an electroluminescent display (EL), a laser—particularly preferable being laser diodes and fiber lasers, a plasma display panel (PDP), a field emission display (FED—an array of miniaturized cathode ray tubes), and a vacuum fluorescent display (VFD).

According to the present invention, the illumination system can especially also include a combination of the "illumination system" and "two-dimensional optical switch" components. Here, an "illumination system" is understood to be an optical system for the even illumination of a specific area. It includes one or more illumination sources and optical components that ensure even illumination, especially (specular) reflectors, lenses, integrators, and other components, such as apertures for limiting the radiant field, and filters for spectral limitation. In this context, "integrators" are understood to be optical components that facilitate homogenizing a light bundle, consisting especially of diffusion discs, for example comprising frosted glass, a microlens system, or a combination of these components with a spherical integrating concave mirror. In particular, an illumination system based on the principle of microscope illuminating optics after Köhler (headword "microscope," Fachlexikon Physik, Verlag Harri Deutsch, Frankfurt a. M. 1989) can be employed. The illumination system can also consist of one or more homogeneous radiant field, constructed, for example, from fiber optic bundles (manufacturer: e.g. Schott-Fostec, Auburn, N.Y., USA).

An optical switch is an optical element whose transmission or reflection can be externally controlled. A two-dimensional optical switch is a two-dimensional-array comprising just such optical switches. According to the present invention, a liquid crystal device (LCD) or a digital micromirror device (DMD, manufacturer e.g.: Texas Instruments, TX, USA) are preferably used for this.

Detection System

The object of the detection system is to identify under illumination those test sites whose probe molecules interact with the organic molecules to be detected, especially those at which a reaction has taken place between these molecules. It preferably comprises one or more detectors and apparatuses for supplying and evaluating the measuring signals. Here, it is expedient to coordinate the detection system with the type of readout method, i.e. the type of photoinduced reaction, of the test system employed:

For the biochips with electrical readout that are particularly preferably employed as the test system, especially DNA chips with direct electrical readout (especially based on patent applications DE 19921940, DE 19926457, and DE 19945398) the detection system preferably comprises a measuring device for determining the electrical communication between the test sites and the conductive surface of the biochip. This measuring device is preferably a current, charge, voltage, or potential measuring device, a cyclovoltammetry device, an amperometry device, or a conductivity measuring device. A cyclovoltammetry device is a measuring device for recording current-voltage curves, the voltage being changed periodically and linearly with time. An amperometry device is a measuring device for recording current-time curves. A conductivity measuring device allows conductivity to be measured, especially by measuring the current at a fixed voltage or by measuring the voltage at a constant current. Biochips with microelectrodes allow spatial limitation of the electrical readout and thus spatial resolution of the measurement, or an electrical readout limited to individual test sites.

In the case of photosensitive biochips with optical readout, the photoinduced reaction of the chip, especially luminescence, is detected optically. Such chips are very popular and are manufactured, for example, by Affymetrix (CA, USA), Nanogen (CA, USA), and Incyte/Synteni (CA, USA). If such optical-readout capable biochips are used as the test system, the detection system expediently comprises an optical detector for detecting the photoinduced reaction of the chip. Advantageously, this detector is a CCD (Charge Coupled Device), an intensified CCD (CCD with an preceding photomultiplier consisting of many tiny metal tubes, thus achieving overall higher sensitivity), a CMOS camera (an optical detector manufactured using CMOS technology—Complementary Metal Oxide Silicon—a distinguishing feature of which is its large optical dynamic range), a photodiode array, a phototransistor array, or one or more photomultipliers (photon detector tubes in which electrons are released, amplified, and detected by photons).

The complete optical construction, consisting of the illumination system and, if applicable, a projection system and an optical detection system, can additionally include mirrors to bend the beam path and thus achieve a different geometry, especially a more compact design.

Overall, a combination of the illumination system described within the context of the present invention, comprising an array of independently addressable illumination sources, and a per se known scanning system is also possible:

In this case, the illumination system is dimensioned such that only part of the photosensitive biochip is illuminated. In a first step, initially this part of the chip is excited and read out. In a subsequent step, either the chip is moved the width of one field via an x-y translation table or the illumination field is moved the width of one field via movable tilted mirrors. Thereafter, the chip region thus newly selected is excited and read out. This process is repeated until the entire chip has been read out. In the case of an illumination system consisting of an array having a limited number of pixels, illumination of the entire chip can be achieved with high pixel density through combination with a scanning process.

If on the other hand the number of pixels in the illumination system is large, it is often expedient to image multiple illumination sources on one test site each time.

Signal Acquisition and Detection Method

In a preferred embodiment, the signal acquired by the detection system is transmitted to an evaluation system, preferably a computer. In this way, error correction, especially correction of potential inhomogeneities in the illumination system, the biochip, or the detection system is also possible. Such inhomogeneities can be caused for example by uneven illumination, process tolerances, and shading and edge effects. The signal captured by the detection system is expediently correlated with the illumination pattern of the illumination system and the type and position of the test sites on the biochip.

In a preferred embodiment, the detection system has no spatial resolution, so that all test sites of the photosensitive biochip at which a photoinduced reaction has occurred are read out together. A preferred example for this embodiment comprises, as the test system, a photosensitive biochip with electrical readout on which all test sites are applied to a common measuring electrode. The addressing of the individual test sites in this embodiment occurs exclusively through test site-specific optical excitation.

In a likewise preferred embodiment, the detection system has one- or two-dimensional spatial resolution that is achieved especially through multiple detector sub-areas (pixels) that can be read out individually. Spatial resolution of the detection system can be achieved for example in the case of electrical readout by means of a biochip on which the test sites are applied to multiple conductive surfaces that can be read out individually, in combination with a measuring device having the appropriate number of test connectors. In the case of optical readout, spatial resolution of the detection system can be realized with a spatially resolving optical detector, especially a CCD, an intensified CCD, a CMOS camera, a photodiode array, or a phototransistor array. Such detection systems with spatial resolution preferably have the same number of pixels as the illumination system. Instead of the same number of pixels, an integer ratio of the number of detection system pixels and illumination system pixels can also be expedient. If such spatially resolving detection systems are used, then, in addition to the correlation of the illumination system's illumination pattern with the type and position of the test sites on the biochip, a correlation with the signal pattern captured by the detection system is also possible.

According to the present invention, the methods described below may be employed to detect organic molecules in a probe substance:

Firstly, a photosensitive biochip including an array of test sites having specific probe molecules is provided as the test system. These probe molecules are preferably specific for the molecules to be detected in the probe substance, or for the interaction to be detected between these probe molecules and the probe substance. For this purpose, a suitable illumination system for optically illuminating the photosensitive biochip is provided, comprising an array of independently addressable illumination sources that are arranged such that to each test site of a sub-array of the test system is assigned at least one illumination source that illuminates substantially only it. After a probe substance has been supplied to the test system, the test sites are illuminated by addressing, according to a preselected pattern, the respective illumination sources assigned to them. Simultaneously, the test sites are examined with a view to whether their probe molecules interact with the organic molecules to be detected.

This identification of this interaction can preferably take place through an electrochemical process, especially through cyclic voltammetry, amperometry, conductivity measurement, or another current, charge, voltage, or potential measurement. In the case of biochips with electrical readout, an identification of the reaction between the probe molecules and the organic molecules to be detected is preferably made possible by arranging the test sites on a conductive surface and the reaction being detected by determining the electrical communication between the test sites and the conductive surface. This communication, in turn, is preferably detected by an electrochemical method, especially through cyclic voltammetry, amperometry, conductivity measurement, or another current, charge, voltage, or potential measurement.

A likewise preferred identification of the reaction between the probe molecules and the organic molecules to be detected is based on an optical process, especially the detection of luminescence.

While in the case of scanning illumination methods according to the prior art, for example employing a laser scanner, typically only one test site can be illuminated at a time, the illumination system described within the context of the present invention allows illuminating multiple test sites simultaneously. As a result, there are a number of illumination patterns to select from. For the detection method described here, an optimum illumination pattern adjusted to the conditions of the detection apparatus can be selected. In particular, multiple test sites, preferably those for which the probability of a reaction with the organic molecules to be detected is low, can first be simultaneously illuminated and read out. If no reaction is detected within such a group, a reaction can be precluded for the entire group and further readout of the individual test sites of this group can be dispensed with. Only if a reaction was ascertained within such a group of test sites, or could not be reliably precluded, is a further illumination and readout of these test sites necessary in a subsequent step, in a different grouping or individually. Since, in the case of such a procedure, entire groups of test sites are in some cases read out simultaneously and can be classified as non-reacting, the overall readout process time can be shortened. For example, in the case of a chip having $N=2^n$ test sites (n is an integer) for which a reaction with the test solution is detectable at only one test site, instead of N readout steps, only $2n+1$ readout steps are necessary if the following readout method is applied: First, all test sites are read out at once, then each half thereof, and thereafter, the half in which a reaction was detected is, in turn, divided into two halves, both of which are read out, the half in which a reaction was detected being iteratively halved until, finally, the test site at which a reaction is detectable is unambiguously identified. In this example, time savings by a factor of $N/(2n+1)$ are also possible, in the case of a chip with 1024 test sites for example, time savings by a factor of 49. If a reaction is detectable at multiple test sites, the time savings are less, since the iteration process must branch.

The illumination pattern can also be optimized with respect to the distances between the test sites, especially in order to minimize, during readout, interactions between test sites in close proximity to one another. Here, for example, in a first step, only every other test site is illuminated, while the remaining test sites are illuminated thereafter in a second step. In the case of strong influences and/or short distances between the test sites, larger gaps between the illuminated test sites can also be expedient.

To increase the sensitivity of the readout method, especially in the case of a strong background signal that is constant or that varies with time, when reading out a test site, its illumination intensity can be varied with time. In particular, a differential measurement (signal with illumination—signal without illumination) is possible. Furthermore, the illumination can be periodically varied with time and the signal (the detected reaction between the probe molecules and the organic molecules to be detected) further processed frequency- or phase-specifically. For this purpose, the signal is processed in an amplifier with a phase-sensitive rectifier (lock-in amplifier) that is triggered synchronously with the pulsating illumination. The rectified signal at the exit of the lock-in amplifier is then a gauge for the reaction initiated by the illumination. In particular, suppression of constant signals or periodic signals whose frequency differs considerably from that of the illumination frequency is possible through such a lock-in process. The frequency used in the lock-in process should differ from any interference frequencies that may exist in the vicinity of the measuring assembly, especially the frequency of the power supply system (50 or 60 Hz) or integer multiples thereof, must be less than the threshold frequencies of the illumination system and detection system used, and lies preferably in the range from 1 Hz to 100 MHz, the upper threshold frequency in miniaturized readout systems also being able to be higher. Especially preferably used are frequencies in the kHz range, for example 3 kHz.

In the case of periodic illumination of the test sites, multiple test sites can also be read out simultaneously by various test sites being illuminated with differing frequencies or phases and the identification of the reaction between the probe molecules of a test site and the organic molecules to be detected resulting with the aid of frequency- or phase-specific signal processing.

In addition to an increase in sensitivity and/or a reduction of the measuring time, a further advantage of periodic illumination and readout of the test sites is improved regeneration ability of the test system. For example, undesired intermediate states produced by optical excitation, especially triplet states of the probes, targets, or other molecules in the vicinity of the test site just addressed, can relax to the normal state in the dark phase. Regeneration can also consist in possible substances converted by the readout process, especially in the vicinity of the test site, especially ions in the case of an electrical readout process, being removed or delivered subsequently.

BRIEF DESCRIPTION OF THE DRAWINGS

The invention is intended to be explained in greater detail below by reference to exemplary embodiments in association with the drawings, wherein:

FIG. 3 shows schematic diagrams of exemplary embodiments according to the present invention, wherein a liquid crystal display (LCD) is used for the illumination system (Embodiment 1).

FIGS. 3A to 3C show apparatuses in which, in addition to illumination optics, a projection system is employed (Embodiment 1a).

FIGS. 3D and 3E show more simply constructed apparatuses with no projection system, in which the biochip is arranged very near the liquid crystal (Embodiment 1b).

FIG. 4 shows schematic diagrams of exemplary embodiments according to the present invention, wherein a digital micromirror device (DMD) is used for the illumination system (Embodiment 2).

FIG. 5 shows schematic diagrams of exemplary embodiments according to the present invention, wherein a video projector is used for the illumination system (Embodiment 3).

MANNER FOR CARRYING-OUT THE INVENTION

Figure 1:
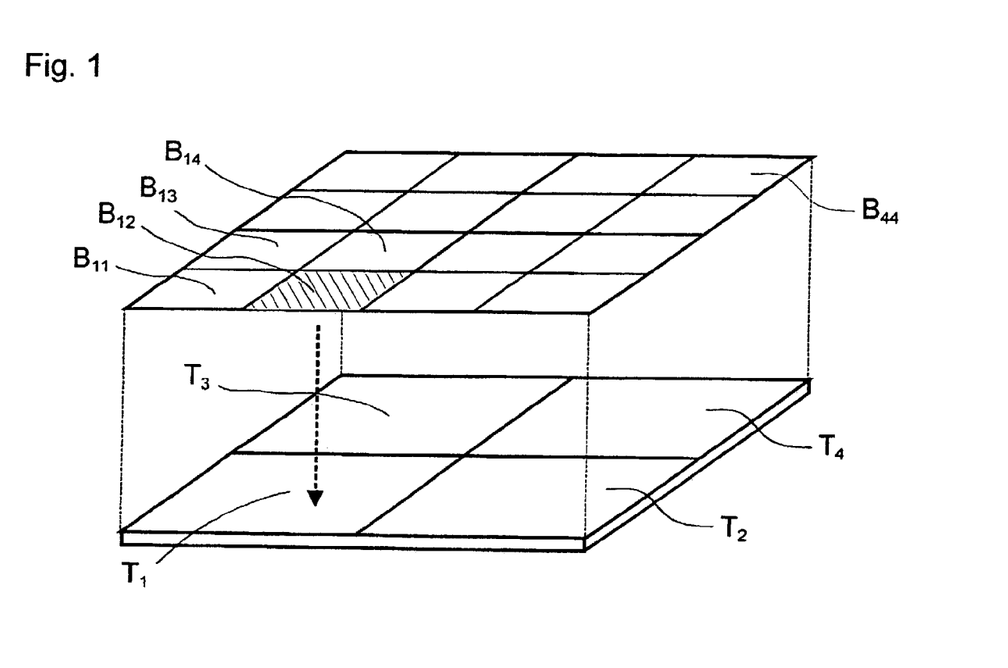
FIG. 1 shows a schematic, perspective diagram of the basic assignment of illumination sources to test sites on the test system.

The operating principle is first explained with reference to FIGS. 1 and 2. The test system of the embodiment in FIG. 1 comprises an array of test sites ($T_1$–$T_4$), each test site exhibiting specific probe molecules. In order to detect organic molecules (targets) in a test solution, the former are supplied to the test system. The test system has the property of showing, when an arbitrary test site is illuminated, a physical reaction that specifically depends on the interaction between the targets and the probes of this test site. An essential feature of the present invention is the illumination of the test sites $T_1$–$T_4$ of the test system with an illumination system, which here comprises an array of illumination sources $B_{11}$–$B_{44}$. To each test site is assigned at least one illumination source that illuminates substantially only it. In the embodiment of FIG. 1, four illumination sources are assigned to each test site, for example sources $B_{11}$, $B_{12}$, $B_{13}$, and $B_{14}$ to test site $T_1$. Their illumination is exemplarily represented by the activated illumination source $B_{12}$.

Figure 2:
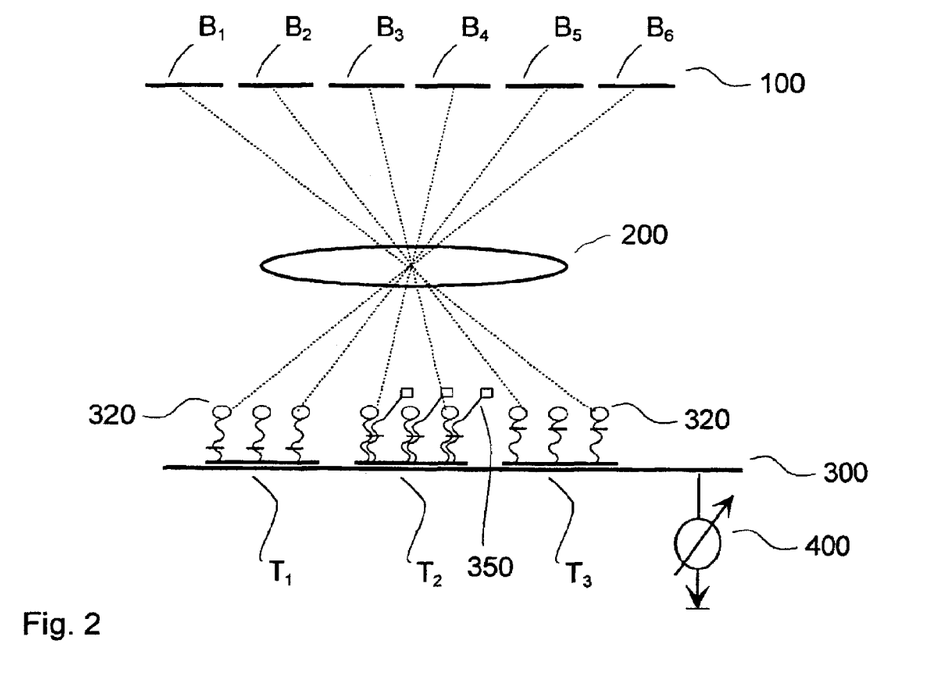
FIG. 2 shows a schematic diagram of the basic construction of the apparatus according to the present invention.

FIG. 2 shows, in a schematic diagram, the basic principle of an apparatus according to the present invention, including an illumination system 100, a projection system 200, a test system 300, and a detection system 400. The illumination system 100 consists of independently addressable illumination sources $B_1$–$B_6$, which can be projected via projection system 200 onto test sites $T_1$–$T_3$ of test system 300. Test sites $T_1$–$T_3$ comprise specific probe molecules 320, which can specifically interact with targets 350 comprising the test solution. Targets 350, which specifically react with the probes of test site $T_2$, are shown for example purposes. Upon illuminating with one of the illumination sources $B_3$ or $B_4$ assigned to this test site, the physical reaction of the test system 300 with the detection system 400 is detected. This physical reaction is, for example, an increased current flow through test site $T_2$, caused by increased conductivity of the specific probes+targets system compared with the unreacted probe molecules. Here, test sites $T_1$–$T_3$ are located on a conductive surface of test system 300. The current flow from the attached molecules across the conductive surface to ground, induced by the illumination, is detected via a current measuring device 400. Here, the reaction of multiple test sites $T_1$–$T_3$ can be detected jointly (as in FIG. 2) or for each test site individually, for example via individually addressable electrodes. If multiple test sites, such as $T_1$–$T_3$ in FIG. 2, are read out via a shared electrode, a test site at which a reaction took place between the probe molecules and the target molecules can be identified through selective illumination:

In the situation of FIG. 2, a current flow results for example at measuring device 400 upon illumination the test system with illumination sources $B_3$ or $B_4$. If, in contrast, only sources $B_1$ and $B_2$ or $B_5$ and $B_6$ are active, there will be no current flow as a result of no reaction occurring at test sites $T_3$ or $T_1$.

In this way, in the case of a specified assignment of illumination sources and test sites, high-resolution detection can also result when reading out the test system with a shared electrode.

Applying individual test sites or groups of test sites to separate electrodes can be practical nonetheless, for example to achieve better selectivity and a better signal-noise ratio or to be able to influence the interaction of probe and target molecules through spatially limited electrical fields.

Preferred Embodiments:

A few special embodiments of the invention will be described in greater detail below with reference to FIGS. 3A to 5C. Individual elements of the apparatuses thereby described can also be combined with one another in a different way. In principle, differing illumination systems 100 can be combined with various projection systems 200 and test systems 300, as well as detection systems 400 suitable for the affiliated readout process. Furthermore, different illumination systems (consisting of the components having reference numbers 101–149) can be combined with various two-dimensional optical switches (150, 160), in particular for constructing an illumination system 100. Moreover, differing detectors can be used; particularly in the embodiments with CCD, this can be replaced by another optical detector, preferably an intensified CCD camera or a CMOS camera.

Type 1 Embodiments: Illumination System with Liquid Crystal (LCD)

A distinguishing feature of a first group of embodiments (FIGS. 3A–3E) is that a liquid crystal device (LCD) 150, as an example of a transmitting optical switch, is used as a two-dimensional optical switch.

The illumination system (101–132) follows the microscope illumination optics after Köhler. It consists of a lamp 101 having a specular reflector 102, an optional integrator 105, a condenser 130, filters 110, and apertures 120/132. The lamp 101, in combination with one or more spectral filters 110, is chosen such that the radiation emitted is spectrally tuned to the biochip 301/302 used. In particular, incandescent lamps, preferably halogen lamps, or arc lamps can be employed for this purpose. The reflector 102, preferably having a parabolic shape, is positioned such that the light emitted from the lamp strikes the integrator 105 at a parallel. The object of the latter is to homogenize the light beam and to ensure even illumination. In particular, diffusion discs, for example comprising frosted glass, or a microlens system can be used for this purpose. The field diaphragm 120 mounted closely behind integrator 105 limits the radiation to an area that is just large enough to illuminate the liquid crystal 150. The condenser 130 consists of a positive lens or a lens system and its object is to image on the liquid crystal 150 the homogeneous radiation field limited by the field diaphragm 120. It has a focal length f1 preferably in the range from 10 to 300 mm, in the exemplary embodiment 100 mm, and is positioned such that the field diaphragm 120 is sharply imaged on the liquid crystal 150. For example, the condenser 130 is arranged exactly in the middle between the field diaphragm and the liquid crystal, at a distance of 2×f1 from each, when an equally sized lateral extension of the field diaphragm 120 and the liquid crystal 150, and thus a magnification of V=1, is chosen. In the case of differing sizes, magnifications not equal to one, preferably in the range V=⅕ to 5, are possible with other distances according to the imaging equations of the condenser 130.

Since the liquid crystal device 150 transmits only polarized light, the illumination system can already include a polarization filter 115, preferably a low-loss polarization filter (polarization recovery plate), preferably arranged near the field diaphragm 120.

The low-loss polarization filter lets a polarization component of the incident light through and acts on polarization components reflected vertically thereto by rotating their polarization directions and reinserting them into the beam path. In this way, overall fewer losses occur during polarization than in the case of a simple polarizer.

Mounted directly in front of the condenser lens 130 is an additional aperture—the condenser aperture 132—for regulating the light intensity of the illumination system.

As a two-dimensional switch in these embodiments, a two-dimensional optical switch to be operated in transmission is employed, exemplarily a liquid crystal element (LCD) 150. It has in both dimensions a pixel number that corresponds to at least the number of matrix elements (test sites) on the biochip to be read out, preferably at least five times as many. The individual pixels and thus, ultimately, the brightness of the illumination system at the relevant position are controlled by a computer control 180. Up to this point, Embodiments 1a and 1b are identical.

Figure 3A:
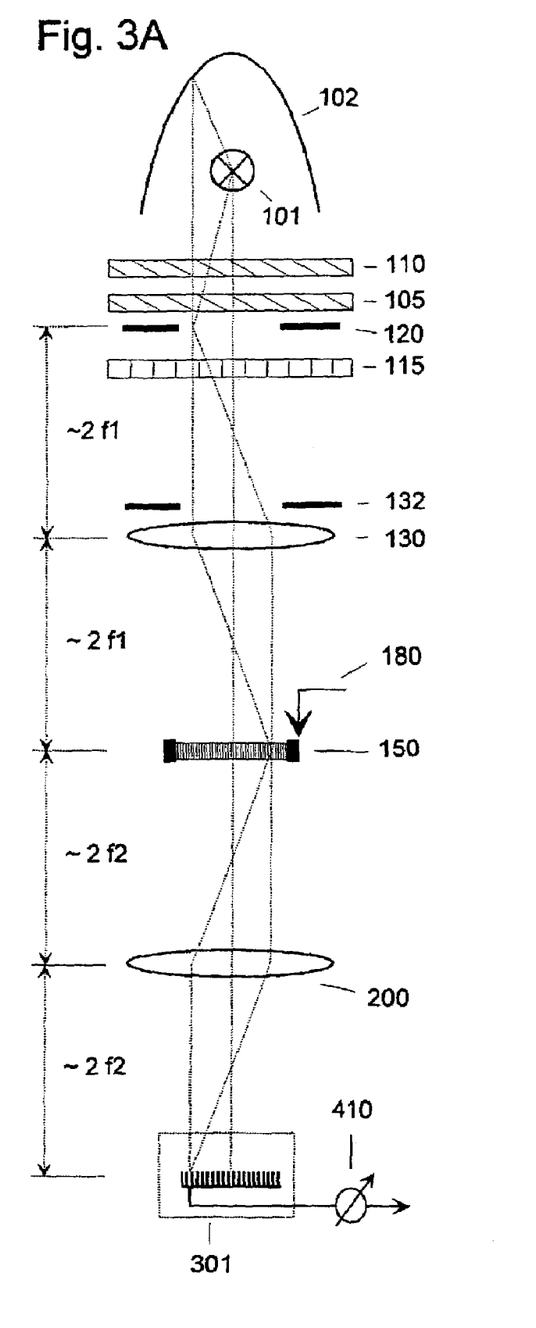
FIG. 3A shows an exemplary embodiment according to the present invention, with LCD, projection system, and electrical detection.
Figure 3B:
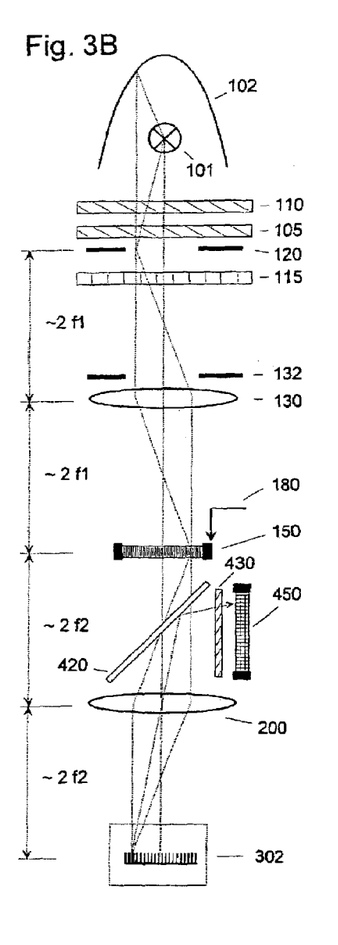
FIG. 3B shows an exemplary embodiment according to the present invention, with LCD, projection system, and optical detection by means of beam splitters.
Figure 3C:
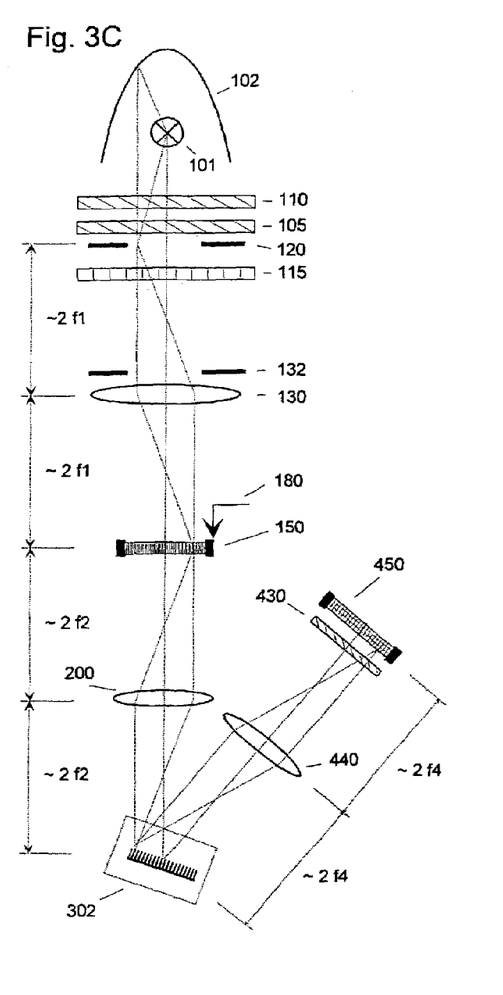
FIG. 3C shows an exemplary embodiment according to the present invention, with LCD, projection system, and optical detection (non-collinear).

The embodiments in FIGS. 3A–3C additionally include a projection system 200 that projects the illuminated LCD 150 onto the biochip 301/302. The projection system 200 consists of a positive lens or a lens system. It is dimensioned and positioned in a manner familiar to a person of skill in the art such that the LCD 150 is sharply imaged on the biochip 301/302 and a magnification is chosen that just facilitates a complete illumination of the chip 301/302. For example, in the case of a biochip 301/302 of size 20 mm×20 mm and an equally sized LCD 150, magnification one is chosen by arranging the projection optics 200 having focal length f2, preferably in the range from 10 to 300 mm, in the exemplary embodiment 100 mm, exactly in the middle between the LCD 150 and the chip 301/302, at a distance of 2×f2 from each. In doing so, the distance between the chip 301/302 and the projection optics 200, and thus also f2, is chosen to be large enough that, for one thing, there is room under the projection optics 200 for the biochip 301/302, with its mounting fixture and any probe supply system that may be connected therewith, and it can be easily replaced. For another thing, the distance is preferably chosen to be considerably greater than the lateral extension of the chip 301/302, such that the incident angle of the illumination beams at various positions on the chip, and thus the illumination intensity, is equal, as far as possible, on every surface unit. However, differences in the illumination intensity can also be corrected by the evaluation software.

The readout of the biochip 301/302 depends on the chip type used. In the case of the particularly preferred electrical readout-capable biochips 301 (FIG. 3A), electrical signals are measured and correlated with the addressing pattern of the LCD 150 by the evaluation software. In this case, no further optical elements are necessary.

For the likewise preferred biochips with optical readout (luminescence chips) 302, an additional optical detection system (420–450) is required (FIGS. 3B, 3C). This consists at least of an optical detector 450, preferably a CCD camera or an intensified CCD camera (manufacturer: e.g. Hamamatsu Photonics, Herrsching, Germany) or a CMOS camera (manufacturer: e.g. Fraunhofer Institute for Microelectronic Circuits and Systems, Duisburg, Germany), in the exemplary embodiment a CCD camera. In front of the detector 450 is mounted an optical filter 430 that is specific for the luminescence wavelength of the biochip 302 and suppresses stray light.

A particularly preferred embodiment (FIG. 3B) further includes between the LCD 150 and the projection optics 200 a beam splitter 420 that, with the aid of the projection optics 200, projects the radiation emitted from the biochip 302 onto the detector 450. If the LCD 150 and the detector 450 are approximately the same size, no further detection optics are required. In this case, the CCD camera 450 is positioned directly in the focus, tilted via the beam splitter 420, of the projection optics 200. If the LCD 150 and the detector 450 are different sizes, a fit to the detector area is ensured by additional detection optics—either included in the CCD camera 450 or as an external optical system (440, see below)—having the appropriate magnification. An increase in sensitivity and suppression of stray light can be achieved through the use of a dichroic beam splitter 420 that has greater transmission at the wavelength of the excitation light than at the wavelength of the light to be detected. Overall, a reversal of the "excitation=transmitted beam" and "detection=reflected beam" assignment is also possible.

A further preferred embodiment (FIG. 3C) is based on a non-collinear arrangement of the excitation and detection beam path (off-axis arrangement). In this way, it is possible to mount separate detection optics 440 independently from the projection optics 200. These optics 440 consist of a positive lens, a lens system, or mirror optics, and are dimensioned such that the biochip 302 is imaged sharply and in full size on the detector 450. Through an optional deviation mirror, the excitation beam path and the detection beam path can be further separated from each other spatially.

Figure 3D:
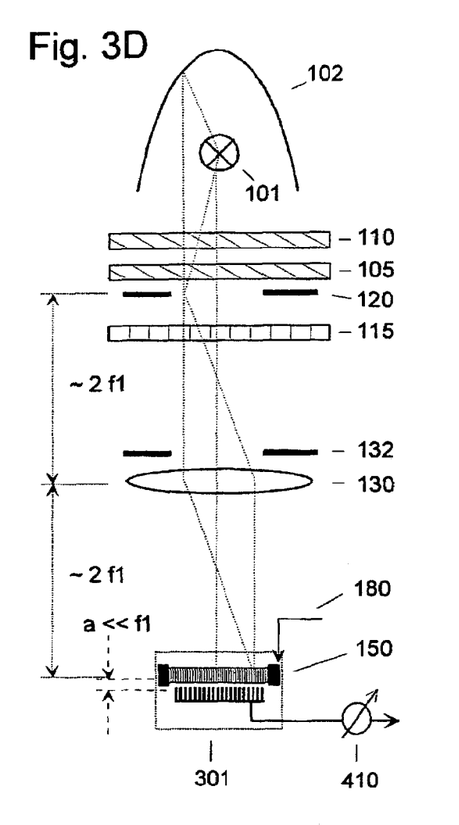
FIG. 3D shows an exemplary embodiment according to the present invention, with no projection system, with LCD and electrical detection.
Figure 3E:
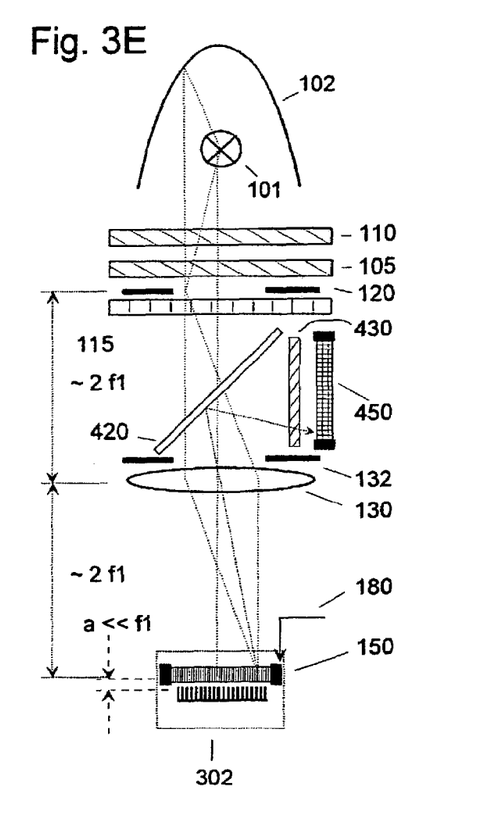
FIG. 3E shows an exemplary embodiment according to the present invention, with no projection system, with LCD and optical detection by means of beam splitters.

In the case of the embodiments in FIGS. 3D and 3E, the projection system 200 is dispensed with. This is possible when the liquid crystal 150 at least is the same size and has the same resolution as the biochip 301/302. In this case, the liquid crystal 150 is arranged directly parallel above the biochip 301/302, such that the illumination pattern of the LCD 150 is projected directly onto the chip. To preclude excitation of adjacent test sites ($T_i$) on the chip 301/302, in this embodiment, the distance a between the LCD 150 and the chip is less than the distance between the test sites on the chip divided by the sine of the exit angle of the excitation light from the LCD.

This embodiment can preferably be employed for electrical readout-capable biochips 301, for which no further optical components (420–450) are required for detecting the reaction of the chip (FIG. 3D). In the case of chips with optical readout 302, in principle, detection of the luminescence via a beam splitter 420 integrated between the condenser 130 and the field diaphragm 120 (FIG. 3E) or with a non-collinear arrangement of excitation beam path and detection beam path is possible—in an analogous manner to that described for Embodiment 1a. Here, however, signal losses due to the double passage through the liquid crystal (excitation and luminescence light) must be accepted, especially in the case of a diagonal passage through the non-collinear arrangement. One advantage in this variant is the greater contrast ratio due to the double passage through the LCD.

Type 2 Embodiments: Illumination System with Digital Micromirror Device (DMD)

A distinguishing feature of Type 2 embodiments (FIGS. 4A–4C) is that a digital micromirror device (DMD) 160, as an example of a reflecting optical switch, is employed as the two-dimensional optical switch. The DMD is an array comprising independently addressable micromirrors, especially like those manufactured by Texas Instruments or the Fraunhofer Institute for Microelectronic Circuits and Systems by means of silicon chip technology. By employing a DMD, high illumination intensity can be achieved with a high fullness factor and contrast ratio. In the case of a two-dimensional optical switch, the fullness factor indicates the ratio of effectively switchable area to total area. Due to gaps between the individual matrix elements, the fullness factor is generally less than 1, but generally higher for a DMD than for an LCD.

Figure 4A:
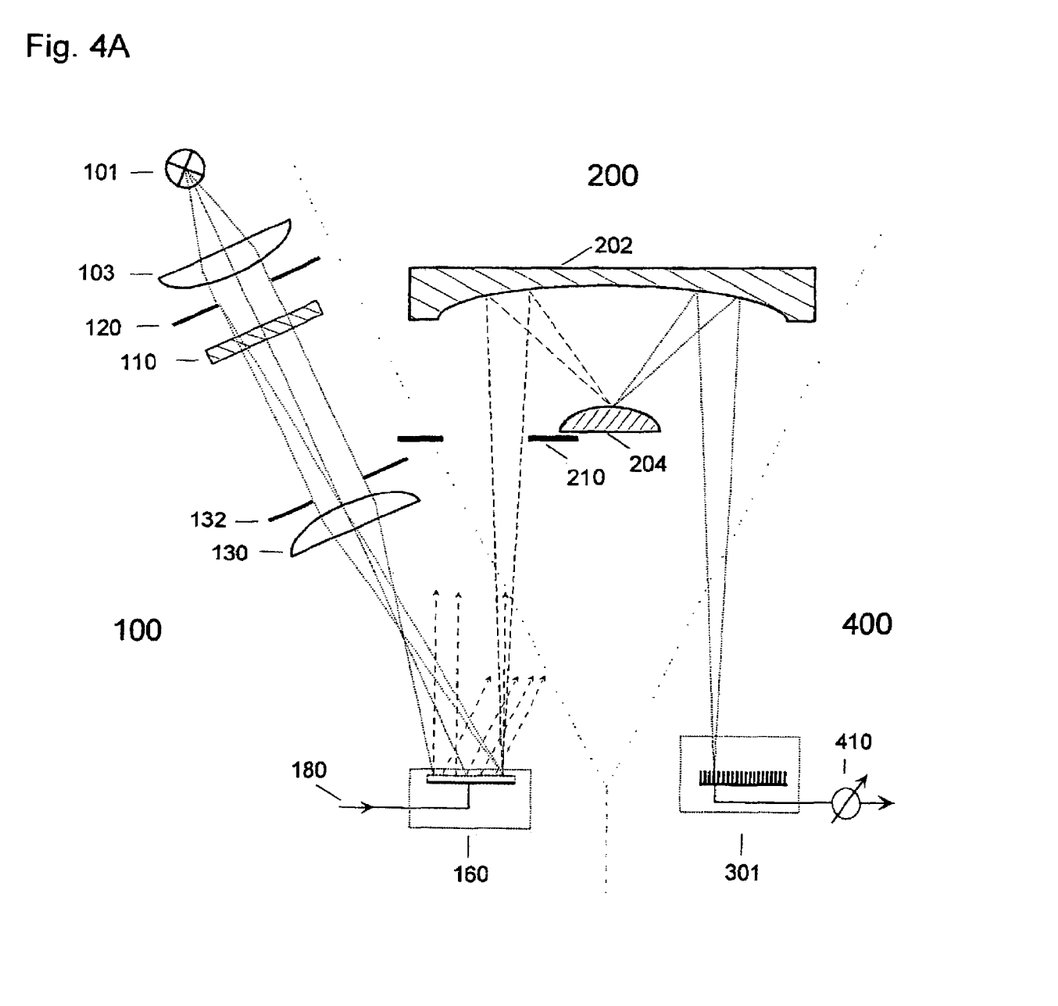
FIG. 4A shows an exemplary embodiment according to the present invention, with DMD, projection system, and electrical detection.
Figure 4B:
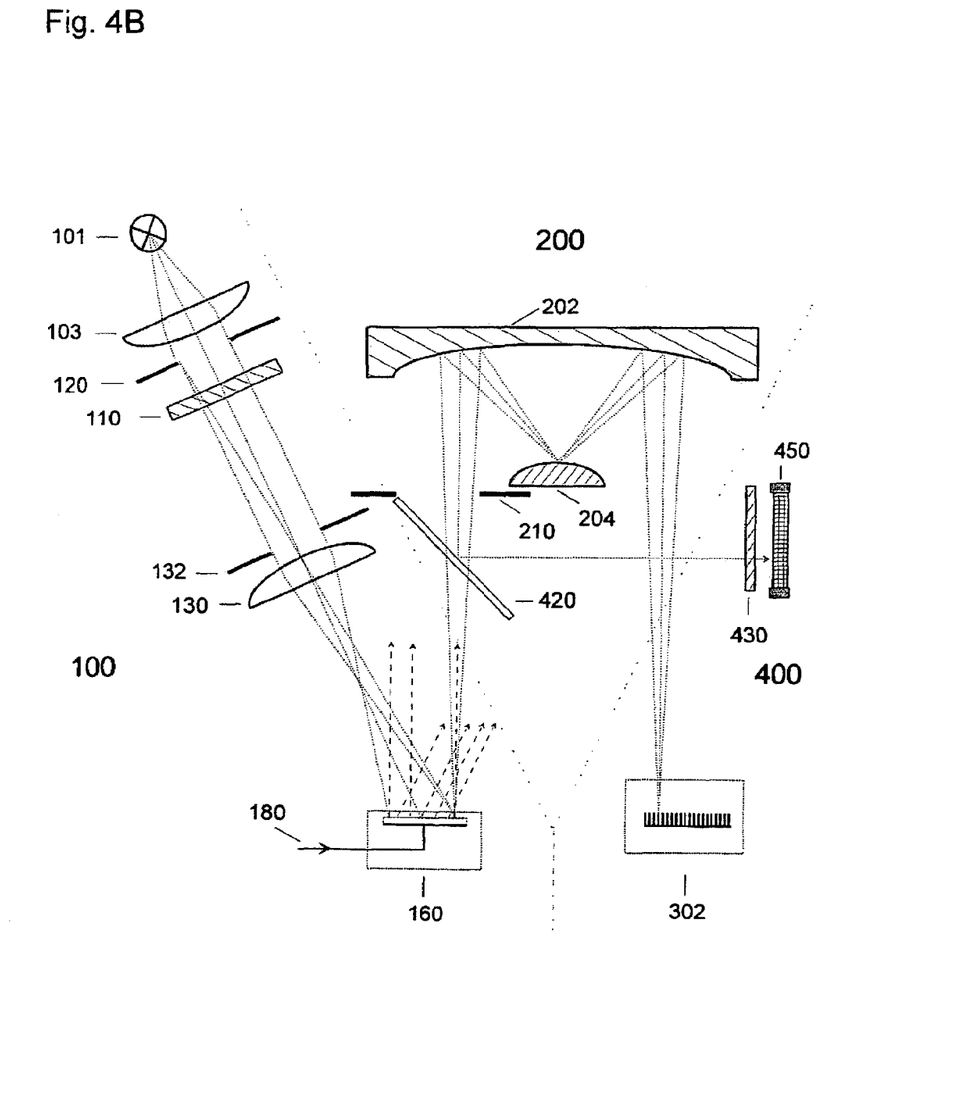
FIG. 4B shows an exemplary embodiment according to the present invention, with DMD, projection system, and optical detection by means of beam splitters.
Figure 4C:
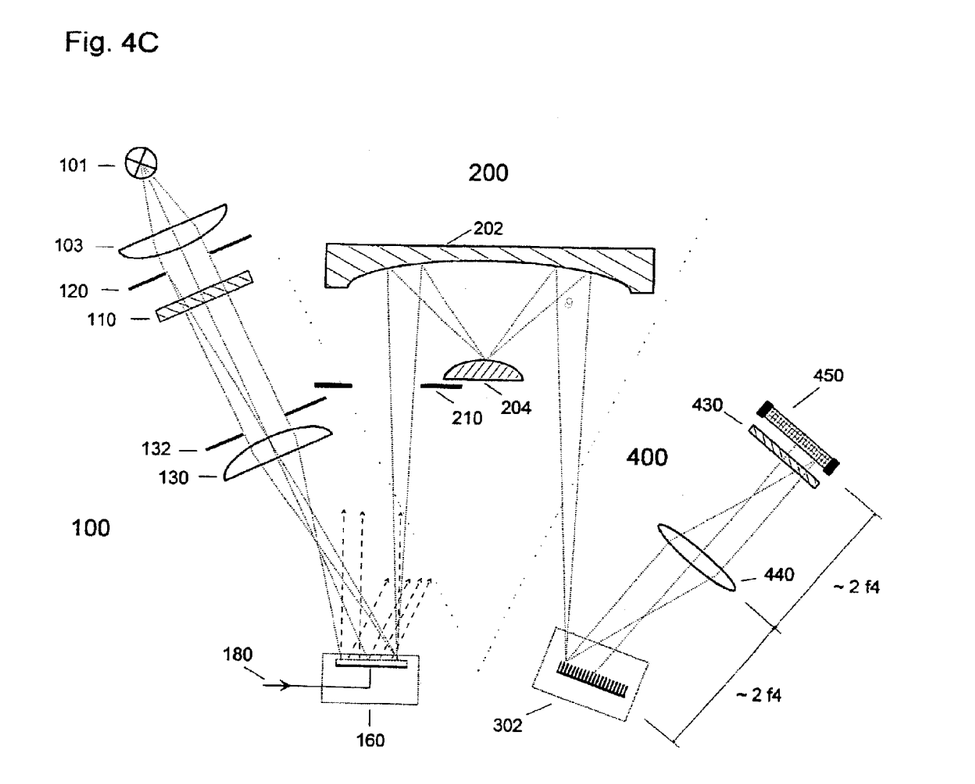
FIG. 4C shows an exemplary embodiment according to the present invention, with DMD, projection system, and optical detection (non-collinear).

The illumination system (101–132) consists of a lamp 101 having a collector lens 103, an optional integrator (105), a condenser 130, filters 110 and apertures 120 and 132. As in the case of the Type 1 embodiments, the lamp 101, in combination with one or more spectral filters 110, is chosen such that the radiation emitted is spectrally tuned to the biochip 301/302 used. The collector lens 103 having a focal length in the range from 20 mm to 200 mm, in the exemplary embodiment 80 mm, is the length of its focal length away from the lamp 101, such that a parallel light beam bundle exits therefrom. This beam bundle is spatially limited by the field diaphragm 120 and can be additionally homogenized by an integrator (105) arranged in front of the field diaphragm.

As in the Type 1 embodiments, the condenser 130 consists of a positive lens or a lens system and its object is to image on the DMD 160 the homogeneous radiation field limited by the field diaphragm 120. Mounted directly in front of the condenser lens 130 is an additional aperture—the condenser aperture 132. Regulation of the light intensity of the illumination system is thus possible.

In the Type 2 embodiments, a two-dimensional optical switch to be operated in reflection, exemplarily a digital micromirror device (DMD, manufacturer: Texas Instruments) 160, is employed as the two-dimensional switch. It has in both dimensions a micromirror number that corresponds to at least the number of test sites ($T_i$) on the biochip 301/302 to be read out, preferably at least five times as many. The individual micromirrors can be inclined and thus, ultimately, the brightness of the illumination system 100 at the relevant position controlled, by a computer control 180.

In contrast to the embodiments in FIGS. 3D,E, in the case of the Type 2 embodiments, a projection system 200 that projects the illuminated DMD 160 onto the biochip 301/302 is required in any case. As an alternative to the projection system 200 illustrated in FIGS. 3A–C, a projection system consisting of mirror optics 202, 204 is generally possible. The projection system after Offner (Optical Engineering, 14 (1975) pp. 130–132) employable here consists of one concave 202 and one convex 204 mirror and images the DMD 160 on the biochip 301/302 in a 1:1 ratio. The necessary magnification factor corresponds to the size ratio between the biochip 301/302 and the DMD 160. Due to the limited numerical aperture of the projection system 200 (e.g. NA~0.08), only light reflected from the micromirrors of the DMD of a specific orientation (active position) reaches the biochip. The more a micromirror is inclined (passive position), the more the excitation light of this pixel is stopped down. To ensure the stop down is defined, the projection system includes a projection aperture 210.

The readout possibilities for the biochip exist as for the embodiments of FIGS. 3A–C. In particular, embodiments with electrical readout (FIG. 4A) and optical readout with beam splitter (FIG. 4B) or non-collinear (FIG. 4C) are possible. In the case of optical readout via a beam splitter 420 (FIG. 4B), the beam splitter is integrated between the DMD 160 and the projection system 200.

Type 3 Embodiments: Illumination System with Video Projector

For the Type 3 embodiments (FIGS. 5A–5C), a video projector 190 is employed as the illumination system. It can be purchased as a complete system, include an LCD (manufacturer: e.g. Philips; Sanyo), a DMD (manufacturer: e.g. Digital Projection, Manchester, UK), or operate according to another principle. When choosing, the following criteria are to be considered: The video projector in Type 3 embodiments has a pixel number (in the exemplary embodiment 800×600) that corresponds to at least the number of test sites on the biochip, a high contrast ratio (greater than 100:1), is focusable on an area the size of the biochip (20 mm×20 mm), exhibits sufficient spatial and temporal stability, homogeneity, and a sufficient illumination intensity in the spectral range suitable for the biochip (especially at 400 nm to 1000 nm), and is computer controllable.

Figure 5A:
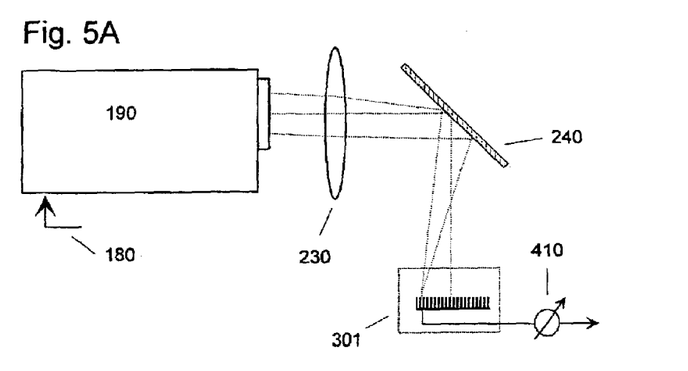
FIG. 5A shows an exemplary embodiment according to the present invention, with video projector, projection system, and electrical detection.
Figure 5B:
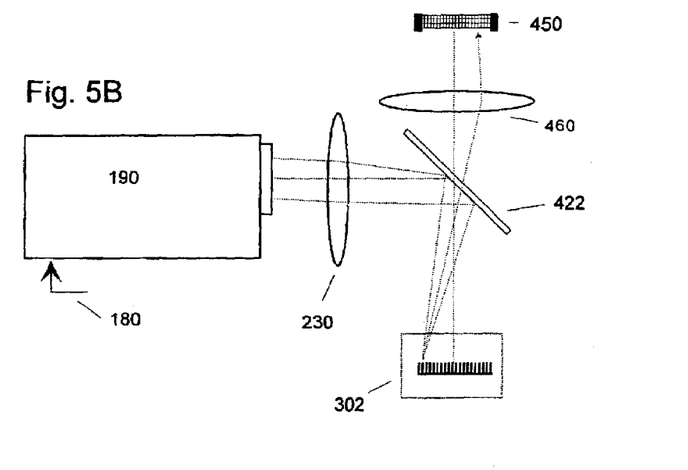
FIG. 5B shows an exemplary embodiment according to the present invention, with video projector, projection system, and optical detection by means of beam splitters.

The image exiting from the video projector is projected onto the biochip 301/302 via a mirror 240 (FIGS. 5A, 5C) or beam splitter 422 (FIG. 5B). An additional projection system 230 is required if no projection of the image onto the size of the biochip is possible with the video projector itself—which is often the case with commercial-quality devices. For biochips with low test-site density (distance between adjacent test sites at least 0.1 mm), the projection system 230 can be realized through a single positive lens (f3=10 . . . 300 mm) (FIG. 3). This produces a sharp image that—in contrast to the usual usage of a video projector—is close (<500 mm) to the projector 190 and small (20 mm×27 mm). The biochip 301/302 can be positioned and optically excited at the site of this image.

Figure 5C:
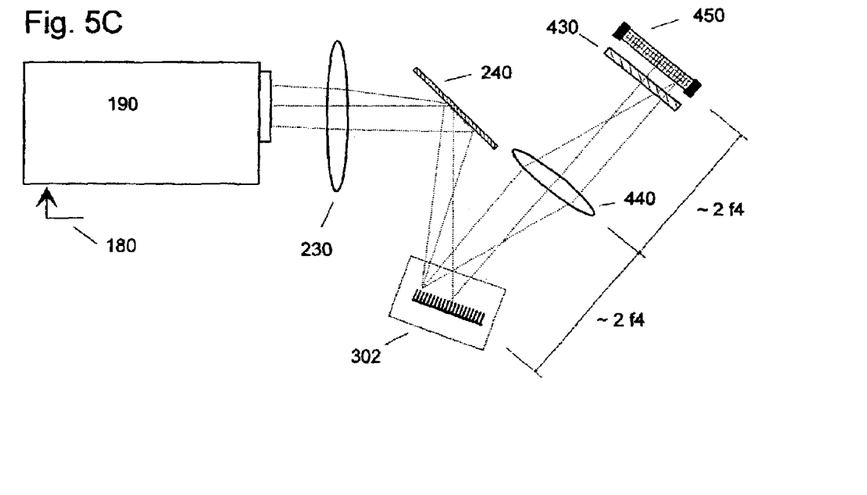
FIG. 5C shows an exemplary embodiment according to the present invention, with video projector, projection system, and optical detection (non-collinear).

A smaller illumination field and thus a higher pixel density can be achieved in a per se known manner through two optical systems. With a first system, an intermediate image (maximum edge length 100 mm) is produced near (<500 mm) the projector. This image is reduced to the size of the biochip 301/302 via a second system.

A further variation of the Type 3 embodiments consists in replacing the projection lens system of the video projector 190, or adjusting it for the specific client, such that a projection onto the size of the biochip 301/302 is possible.

In the case of the embodiments with a video projector, the readout possibilities for the biochip 301/302 likewise exist as for the embodiments in FIGS. 3A–C. In particular, embodiments with electrical readout (FIG. 5A) and optical readout with beam splitter (FIG. 5B) or non-collinear (FIG. 5C) are possible. In the case of optical readout via a beam splitter 422 (FIG. 5B), detection optics 460 are employed in the embodiment with video projector 190 to image the biochip 302 on the optical detector 450.

Increasing the Resolution in All Three Embodiments

If the number of pixels in the two-dimensional optical switch 150/160 or in the video projector 190 is not sufficient to excite the biochip 301/302 with the desired resolution (at least the distance between the test sites on the chip), then the chip can additionally be scanned: to do this, the image of the illumination system 100 is reduced on only a portion of the chip 301/302 such that the desired resolution is achieved. In a first step, initially this part of the chip is excited and read out. In a subsequent step, either the chip is moved the width of one image via an x-y translation table, or the image is moved the width of one image via movable tilted mirrors. Thereafter, the chip region thus newly selected is excited and read out. This method is repeated until the entire chip 301/302 has been read out.

The invention claimed is:

1. A method for detecting organic molecules in a probe substance, with the following process steps:
   providing a test system (300) comprising an array of test sites (T), each test site having specific probe molecules (320);
   providing an illumination system (100) for optically illuminating the array of test sites, the illumination system comprising an array of independently addressable illumination sources (B) that are arranged such that to each test site (T) of a sub-array of the test system (300) is assigned at least one illumination source that illuminates substantially only it;
   supplying the probe substance to the test system (300);
   illuminating the test sites (T) by addressing the respective illumination sources (B) assigned to them, according to a preselected pattern wherein, in at least one step, multiple test sites are illuminated simultaneously;
   reading out all illuminated test sites together after each step of the illumination pattern with a detection system (400) having no spatial resolution; and
   identifying those test sites (T) whose probe molecules (320) interact with the organic molecules (350) to be detected.

2. The method according to claim 1, wherein the test sites (T) whose probe molecules (320) interact with the organic molecules (350) to be detected are identified by an electrochemical method, including a current, charge, voltage, or potential measurement, cyclic voltammetry, amperometry, or a conductivity measurement.

3. The method according to claim 1 or 2, wherein the test sites (T) are arranged on at least one conductive surface and the test sites at which a reaction occurred between the probe molecules (320) and the organic molecules (350) to be detected are identified by determining the electrical communication between the test sites and the conductive surface.

4. The method according to claim 2, wherein the test sites (T) whose probe molecules (320) interact with the organic molecules (350) to be detected are identified by an optical method, including through a detection of luminescence.

5. The method according to claim 1, wherein the pattern for addressing the illumination sources is selected depending on the probability of interaction between the probe molecules (320) of the relevant test site (T) and the organic molecules (350) to be detected by simultaneously illuminating many test sites (T) if the probability of interaction is low, and simultaneously illuminating only one test site or a few test sites if the probability of interaction is high.

6. The method according to claim 1, wherein the pattern for addressing the illumination sources is selected such that no adjacent test sites (T) are illuminated simultaneously or the distances between simultaneously illuminated test sites are as large as possible.

7. The method according to claim 1, wherein the test sites (T) are illuminated periodically and the identification of the reaction is done utilizing frequency- or phase-specific signal processing.

8. The method according to claim 1, wherein various test sites (T) are illuminated periodically with differing frequencies or phases and the identification of the reaction is done utilizing frequency- or phase-specific signal processing.

9. The method according to claim 1, wherein the detected signals are evaluated by means of electronic data processing, in particular, such that corrections may be carried out using characteristic parameters of the apparatus.

10. The method according to claim 1, wherein the sub-array of test sites (T) comprises the entire test site array.

11. The method according to claim 1, wherein the sub-array of test sites (T) includes only a subset of the test sites on the test system (300) and wherein, through a relative movement between the illumination system (100) and the test system (300), all test sites of the test system are successively illuminated and examined for their light-induced reaction.

12. An apparatus for carrying out the method according to claim 1, comprising:
   a test system comprising an array of test sites to which the probe substance can be supplied, each test site having specific probe molecules;
   an illumination system for optically illuminating the array of test sites, comprising an array of independently addressable illumination sources that are arranged such that to each test site of a sub-array of the test system is assigned at least one illumination source that illuminates substantially only it;
   means of supplying the probe substance to the test system;
   means of addressing, according to a preselected pattern, the respective illumination sources assigned to the test sites, which means are arranged and adapted to simultaneously illuminate multiple test sites in at least one step of the illumination pattern,
   a detection system having no spatial resolution, for reading out all illuminated test sites together after each step of the illumination pattern; and
   means of identifying those test sites whose probe molecules interact with the organic molecules to be detected.

13. The apparatus according to claim 12, wherein the detection system comprises a current, charge, voltage, or potential measuring device, a cyclovoltammetry device, an amperometry device, or a conductivity measuring device.

14. The apparatus according to claim 12, wherein the test sites are arranged on at least one conductive surface and the detection system comprises a measuring device for determining the electrical communication between the test sites and the conductive surface.

15. The apparatus according to claim 12, wherein the detection system comprises an optical detector for optically detecting a light-induced reaction of the test system.

16. The apparatus of claim 15, wherein the optical detector is capable of detecting light emitted from the test system.

17. The apparatus according to claim 12, wherein the means of addressing the illumination sources according to a preselected pattern is arranged and adapted to take into account the probability of interaction between the probe molecules of the respective test site and the organic molecules to be detected by simultaneously illuminating many test sites if the probability of interaction is low, and simultaneously illuminating only one test site or a few test sites if the probability of interaction is high.

18. The apparatus according to claim 12, wherein the means of addressing the illumination sources according to a preselected pattern are arranged and adapted to not simultaneously illuminate adjacent test sites or to simultaneously illuminate-test sites arranged as far apart as possible.

19. The apparatus according to claim 12, wherein the means of addressing the illumination sources are adapted to periodically illuminate the test sites, and the means of identifying the test sites whose probe molecules interact with the organic molecules to be detected comprise frequency- or phase-specific signal processing means.

20. The apparatus according to claim 12, having a data processing system for storing, evaluating, and displaying the detected reactions.

21. The apparatus according to claim 12, further comprising an optical system for imaging the illumination system on the test system such that for each test site of the sub-array, at least one of the illumination sources assigned to it is imageable on said test site.

22. The apparatus according to claim 12, wherein the illumination system is disposed substantially parallel to the test system and at such a short distance therefrom that the radiation emitted from each illumination source assigned to a test site illuminates substantially only this one test site.

23. The apparatus according to claim 12, wherein the illumination system comprises a illumination element selected from the group consisting of a cathode ray tube, an LCD display element, a TFT-LCD display element, a field-emission display element, an electroluminescent display element, a plasma screen; a polymer display element, an LED array, an illuminated spatial light modulator, a digital micromirror device, a vacuum fluorescent display, a laser array, and a video projector.

24. The apparatus according to claim 12, wherein the sub-array of test sites T comprises the entire test site array.

25. The apparatus according to claim 12, wherein the sub-array of test sites includes only a subset of the test sites on the test system and, additionally, comprises movement means facilitating a relative movement between the illumination system and the test system.

26. The apparatus according to claim 25, wherein the movement means includes a translation table or a movable tilted mirror.

27. The method according to claim 1, wherein the organic molecules includes biomolecules or polymers.

* * * * *